(12) United States Patent
La Rosa et al.

(10) Patent No.: US 8,283,657 B2
(45) Date of Patent: Oct. 9, 2012

(54) ALL-ORGANIC SENSOR/ACTUATOR SYSTEM

(75) Inventors: Manuela La Rosa, Giarre (IT); Luigi Fortuna, Siracusa (IT); Salvatore Graziani, Nicolosi (IT); Donata Rosaria Maria Nicolosi, Catania (IT); Giovanni Sicurella, Mascalucia (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 270 days.

(21) Appl. No.: 12/636,556

(22) Filed: Dec. 11, 2009

(65) Prior Publication Data
US 2010/0148164 A1 Jun. 17, 2010

(30) Foreign Application Priority Data
Dec. 15, 2008 (IT) .............................. VA2008A0062

(51) Int. Cl.
*H01L 51/05* (2006.01)
(52) U.S. Cl. ........................................ 257/40; 257/415
(58) Field of Classification Search .............. 438/14–18, 438/E51.005–E51.006; 257/414, 40, E51.002
See application file for complete search history.

(56) References Cited

U.S. PATENT DOCUMENTS

| | | | |
|---|---|---|---|
| 4,104,672 A * | 8/1978 | DiLorenzo et al. ........... | 257/275 |
| 5,556,700 A | 9/1996 | Kaneto et al. | |
| 6,475,639 B2 * | 11/2002 | Shahinpoor et al. .......... | 428/614 |
| 7,449,758 B2 * | 11/2008 | Axelrod et al. ............... | 257/415 |
| 2006/0266981 A1 * | 11/2006 | Asaka et al. .................. | 252/500 |
| 2007/0139167 A1 * | 6/2007 | Gilson et al. ................. | 340/407.1 |
| 2008/0197345 A1 * | 8/2008 | Kim et al. ..................... | 257/40 |
| 2009/0032394 A1 | 2/2009 | Wu et al. | |
| 2010/0190285 A1 * | 7/2010 | Stark et al. ..................... | 438/50 |

OTHER PUBLICATIONS

Zhou et al., "Solid state actuators based on polypyrrole and polymer-in-ionic liquid electrolytes," Electrochimica Acta 48:2355-2359, 2003.

* cited by examiner

*Primary Examiner* — Marcos D. Pizarro
*Assistant Examiner* — Suian Tang
(74) *Attorney, Agent, or Firm* — Seed IP Law Group PLLC

(57) ABSTRACT

A sensor and/or actuator system in which functional circuitry is embedded in an all organic electromechanical transducer device is disclosed. The electromechanical transducer device exploits the behavior of a flexible sensible ionomeric material sheet as effective sensing or actuating member sandwiched between flexible organic electrodes when undergoing a deformation or being polarized at a certain drive voltage applied to the, electrodes, respectively. The completely embedded all organic system is realized with a process exploiting relatively low cost deposition and patterning techniques. The enhanced flexibility makes the all organic device suitable for new applications in fields ranging from biomedical to aerospace industry.

22 Claims, 14 Drawing Sheets

Gate dielectric       Filling dielectric

Organic semiconductor    Organic conductor

☒☒ Ion-Exchange Perfluorinated Membrane
☐ Organic Conductor

ALL-ORGANIC SENSOR/ACTUATOR SYSTEM

BACKGROUND

1. Technical Field
2. Description of the Related Art

Organic thin films have been extensively investigated to realize different kind of devices in many application fields such as sensors, actuators and electronic circuit components; in particular, organic semiconductors, have been used as active layer in organic thin film transistors (OTFT), in RF-ID, large-area flexible displays, in optoelectronic devices such as organic light emitting diodes (OLED) and organic solar cells. Moreover, in the interest to produce biomimetic devices many electromechanically active materials, i.e., materials changing their shape when subjected to an input signal or producing an output signal when subjected to force or bending, have been studied. Among these kind of "smart materials", electroactive polymers (EAP) have been extensively investigated and used to realize electromechanical devices with sensing and actuating capabilities. Among EAPs, ionic polymer metal composites and conducting polymers have been largely investigated to realize biomimetic sensors actuators and artificial muscles. Ionic polymer metal composites (IPMCs) generally consist of a thin polymeric membrane having a thickness of about 200 μm, coated, generally through an electroplating process, with noble metal electrodes, generally platinum, with a thickness of 5-10 μm. When a voltage is applied to these electrodes, the IPMC bends, while, when a displacement is applied a voltage is measured from the electrodes.

U.S. Pat. No. 6,475,639, entitled "Ionic Polymer Sensors and Actuators", of Shahinpoor et al. describes methods of making the same for applications requiring sensing, actuating and displacement control. In this case the devices are realized by using the IPMC that are polymer metal composites, therefore the devices are characterized by a metallic coating of the membrane, forming at least one electrode.

Malone et al. [1,2] explored the possibility to use IPMC and Conducting polymers as active materials to freeform fabricate actuators. They synthesized strips of CP actuators trough electropolymerization from a liquid electrolyte containing the monomer, by growing the polymer film starting from their dispersion. In particular, polypyrrole (Sigma-Aldrich), and of PEDOT/PSS (Sigma-Aldrich) dispersion in liquid electrolyte were investigated. Moreover in order to obtain air-operable actuators, they used either a "solid polymer electrolyte" (SPE) which contains some liquid to allow ion migration, or a liquid electrolyte surrounded by some kind of encapsulation.

On another account, thin-film and printed batteries with their customizable shapes, flexible form factors and ultra-low weight are enabling new functionality to be added to a broad range of electronic products, such as smart cards, RFID and sensors both increasing their usefulness and the size of their addressable markets.

For these reasons many companies are investing in printable batteries and photovoltaic research. Varta has developed a 3 V extremely flat lithium-polymer primary cell for use in smart cards. It is embedded in a plastic card with thickness of 0.4 mm and provides a capacity of 25 mAh. Solycore. Inc. has also developed an ultra-thin flexible lithium-polymer battery (Flexion), giving a nominal voltage of 3 V and a capacity of 10 mAh up to 50 mAh and a thickness of 0.37 mm-0.45 mm.

BRIEF SUMMARY

The applicants have found that many of the requisites and of would-be beneficial features of a transducer based on the peculiarities of an ion exchange polymeric sheet or membrane, to be employed in a broad spectrum of useful applications, are most effectively provided by realizing an all organic device that, in its basic form, is constituted by a sheet of a suitably hydrated ion exchange polymeric material, sandwiched between a first electrically conductive layer of an electrically conductive organic material coupled to a first or top surface of the sheet and by a second electrically conductive layer of an electrically conductive organic material coupled to the opposite or bottom surface of the sheet. The sandwich may then have its perimeter edges sealed by a dielectric resin for preventing dehydration of the sensible ion exchange polymeric material core sheet.

The all organic basic device may, in a purposely dedicated area thereof, integrate specific functional circuits, including active components, entirely made with organic materials, thus realizing an all organic system, eventually incorporating also a plastic encapsulated battery.

An all organic integrated system according to this disclosure is particularly useful as a sensor of deformation of the sensible flexible sandwich structure constituted by the sheet of ion exchange polymeric material and the first electrically conductive layer and second electrically conductive layer laminated over the opposite surfaces of the ion exchange sheet, and/or as actuator of deformation of the same structure by applying an electrical voltage to the conductive layers.

BRIEF DESCRIPTION OF THE SEVERAL VIEWS OF THE DRAWINGS

Sizes and relative dimensions of geometrical details of the various structural drawings are not in scale. The figures are for illustrative purposes only and do not imply limitations to the innumerable different geometries with which the disclosure may be practiced.

DETAILED DESCRIPTION

Practical embodiments of the disclosure are described herein below for purely illustrative purposes, alternatives in the choice of organic materials and in the illustrated arrangements of parts being possible and dictated by the particular requisites of the application.

In the embodiments described, the sensible sheet of ion exchange polymeric material may be any commercially available per-fluorinated ionomeric ion exchange membrane, such as Nafion 115 or Nafion 117, produced by Du Pont de Nemours, Flemion, produced by Asahi Glass, Aciplex, produced by Asahi Chemical, and equivalent products. These membranes as commercialized, eventually require to be subjected to a hydration treatment and then to a substitution treatment to replace protons (H+) in pendant polar groups of the per-fluorinated polymeric skeleton with a different cation, usually with Na+ or Li+ in order to develop their electro-chemical and mechanical properties.

Figure 1:
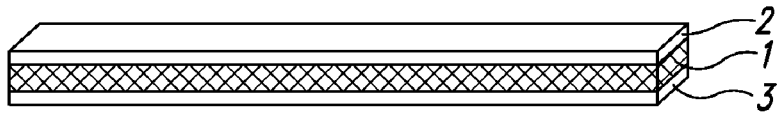
FIG. 1 shows an all organic $IP^2C$ sensing/actuating element of this disclosure.

As depicted in FIG. 1, according to one embodiment of this disclosure, the three layer ionic polymer/polymer composite does not include any metallic layer, whether in form of a dispersed particle layer or else, of known sensible elements, by contrast the flexible sensible element 1 is in the form of an all-organic sandwich composed of a core or central sheet of an ion exchange polymeric material over the opposite surfaces of which are coupled, in other words intimately joined thereon, first and second layers, 2 and 3, of electrically conductive organic material, briefly referred to in the present context also with the acronym IP²C.

The organic conductive material of layers 2 and 3, may be a polymer, such for example PEDOT/PSS or Polyaniline (PANI), or a small molecule resin such for example pentacene and its derivatives, but it may also be a hybrid material.

Moreover, according to a preferred embodiment, realization of complete all-organic devices with sensing and/or actuation circuitry for one both functionalities, integrated with the all organic sensible element of FIG. 1, for providing control signals and power supply, is contemplated.

Figure 2:
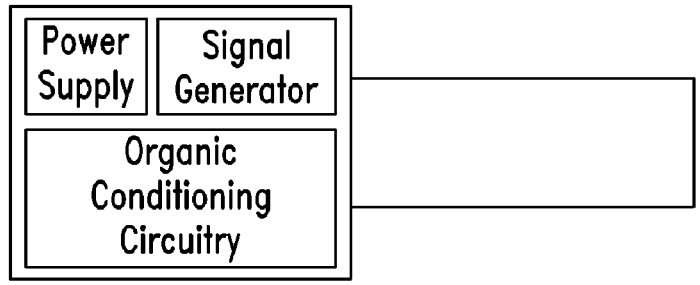
FIG. 2 shows layouts of constituent functional parts of a complete all-organic integrated actuator system according to this disclosure.
Figure 2:
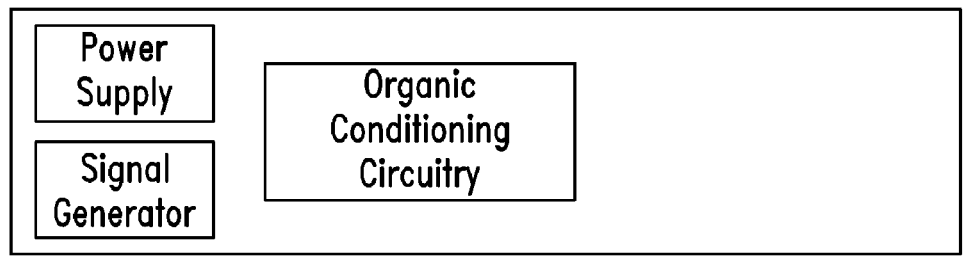

FIG. 2 schematically depict possible layouts of the constituent functional parts related to an embodiment of an all-organic actuating device according to this disclosure.

The active and passive devices constituting the signal generator circuit and the organic conditioning circuitry are all-organic; in particular, organic thin film transistors (OTFTs), organic thin film resistors (OTFR) and organic thin film capacitors (OTFC) are used.

The organic signal generator may be, for example, a fixed signal generator or a voltage controlled oscillator.

The organic conditioning circuitry may comprise a current buffer for supplying the actuator device i.e., the IP²C strip or tail part of the device of FIG. 2, with adequate current to produce the desired deflection or deflecting force in the core sheet of ionomeric ion exchange material.

The organic conditioning circuitry, the signal generator and the power supply may be realized over a IP²C substrate or alternatively directly over a suitably shaped end portion of the IP²C structure itself.

A feature of organic materials is their ability to be processed starting from solutions. This allows use of relatively low cost deposition techniques such for example spin-coating, dip-coating and drop-casting, moreover it allows use of low cost manufacturing techniques such inkjet printing (IJP), soft lithography (SL) and nano imprint lithography (NIL). In the context of this disclosure, each layer constituting the all organic device can be deposited from liquid phase or pre-formed solid phase layers and liquid phase deposited layers may be used.

An IP²C device realized according to a basic embodiment of this disclosure may be realized by coating the opposite major surfaces a strip of solid phase Nafion with liquid phase PEDOT/PSS by spin-coating. According to an alternative embodiment, all layers may be deposited from liquid phase in succession using for example a liquid Nafion dispersion, liquid phase organic conductors, dielectrics, semiconductors and isolation resins.

Figure 3:
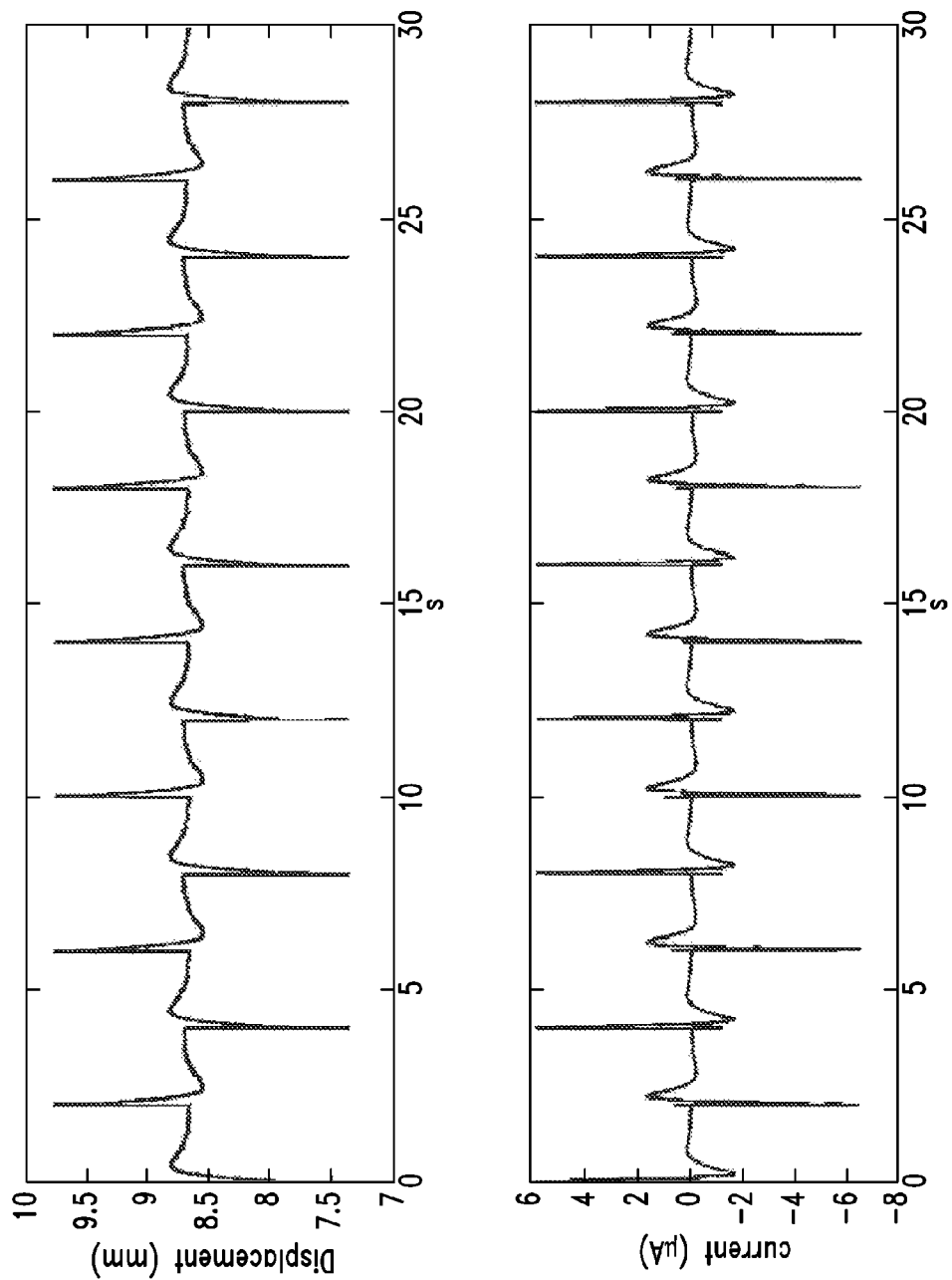
FIG. 3 shows the sensing response of a cantilever held, all-organic $IP^2C$ sensor device subject to impulsive impacts.

FIG. 3 shows the sensing response output current produced by an IP²C device in cantilever configuration when subject to impulsive impacts causing an impulsive alternated deflection of a sensible composite according to the above described first embodiment and held at one end in a cantilever fashion, by about 1 mm, in both directions. The output current was measured by means of a high gain current-voltage converter amplifier.

Figure 4:
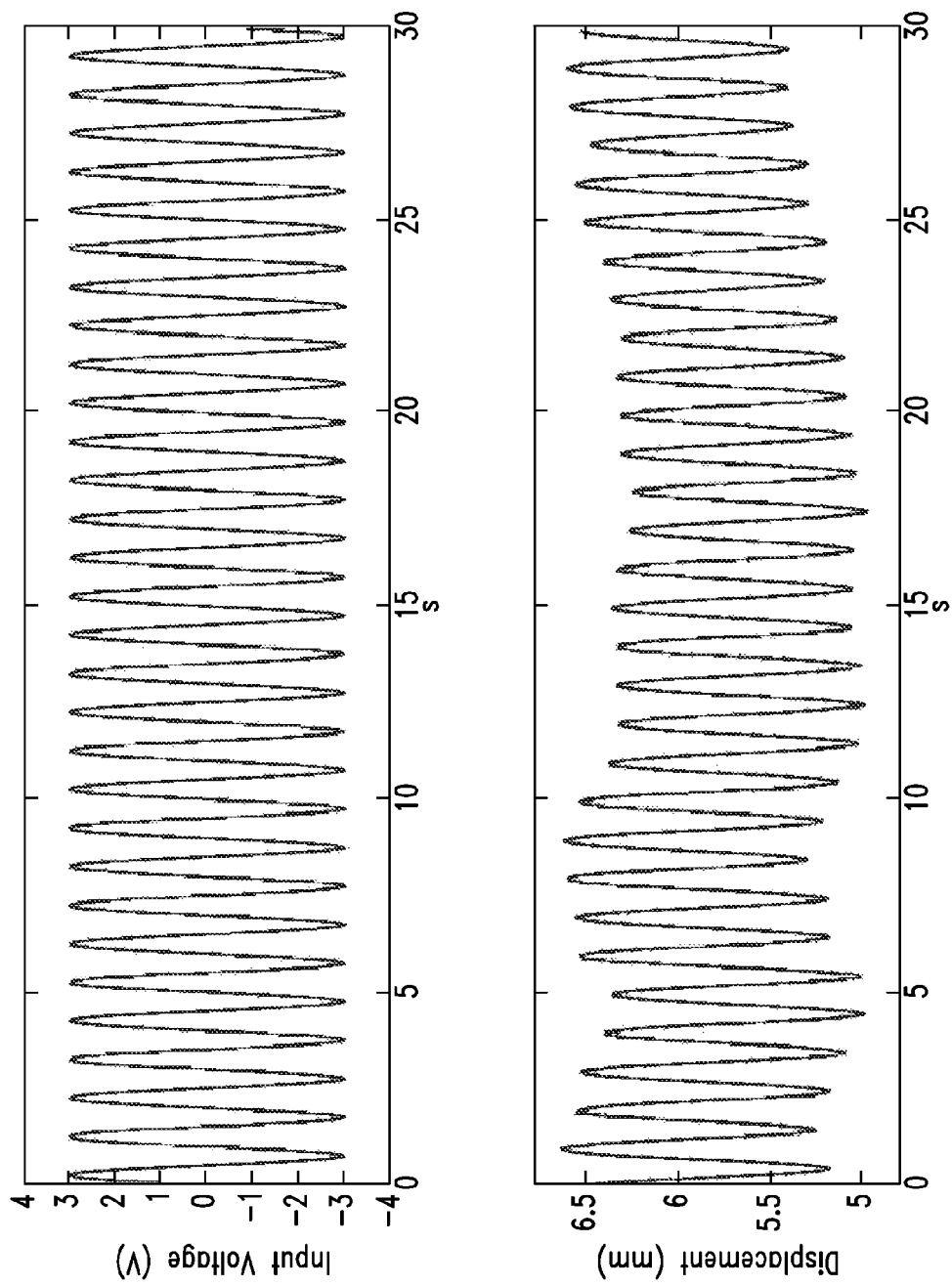
FIG. 4 shows the displacement obtained from the same cantilever held $IP^2C$ device when functioning as an actuator by applying a sinusoidal drive voltage to its plate electrodes.

FIG. 4 shows the displacement obtained from the same IP²C device held in cantilever fashion, when working as an actuator by applying to the electrically conductive organic layers formed over the opposite surfaces of the Nafion strip, a sinusoidal drive voltage of 4 V peak-to-peak, at the frequency of 1 Hz.

In a completely integrated form, that is incorporating a DC power source that may be a plastic encapsulated micro battery and circuitry configured for the intended application of the IP²C device, typically as a sensor and/or as an actuator, the all organic device of this disclosure may be useful for innumerable applications. Just to mention few, the device may be used as a sensor indicating structural displacements, generating for example a luminous signal.

Figure 5:
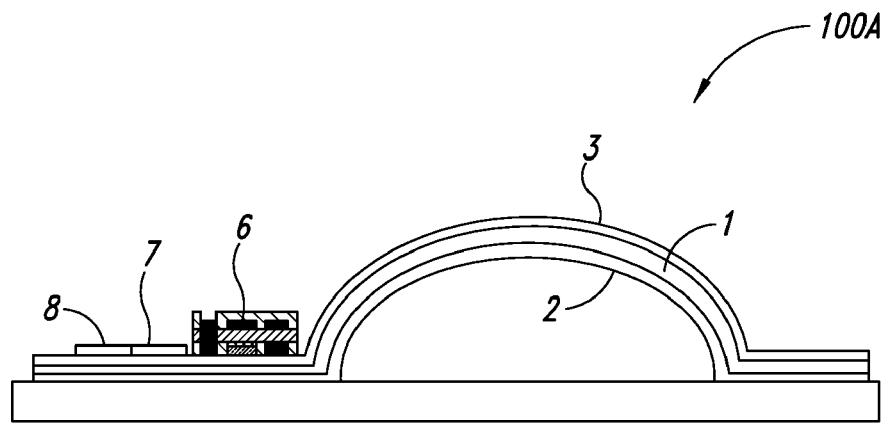
FIG. 5 is a simplified schematic illustration of an $IP^2C$ motion sensing device.

As schematically depicted in FIG. 5, an IP²C motion sensing device 100A may comprise a multilayer membrane composed of a sensible ionomeric core sheet 1 of suitable ion exchange resin and opposite organic conductor resin layers 2 and 3, over a part of which are realized the organic circuitry 6 of signal sensing and conditioning, an organic LED (OLED) 8 to signal the sensed variation, and the power supply 7, typically in the form of a micro primary battery or of a contactless rechargeable secondary battery.

Of course any all organic IP²C device of this disclosure may be completely coated by a flexible film of an isolating and eventually transparent plastic that encapsulates the device, in order to ensure that it withstands the environment and/or its biocompatibility in case of biomedical applications.

Figure 6:
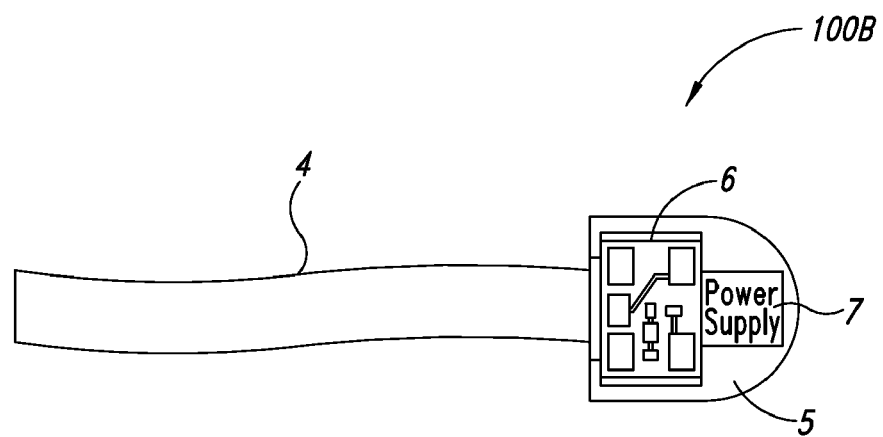
FIG. 6 shows an all-organic robotic swimming structure made according to the present disclosure.

Another possible embodiment of the all organic IP²C device of this disclosure is for a robotic swimming structure 100B, as that shown in FIG. 6, in which a "tail" portion 4 of the three layered membrane, electrically driven by the all organic circuit 6 is swayed rhythmically in a liquid environment for propelling the structure. The "head" portion 5 containing the drive and conditioning circuitry of the structure and the power source, may be realized at one end of the same membrane strip or over a different plastic substrate attached to one end of the elongated membrane (swayable tail). The all organic circuitry, comprising the signal generator and conditioning circuit and the power supply connects to the opposite surface electrodes (conductive layers 2 and 3) of the three layer membrane. The complete device may be eventually encapsulated in a flexible plastic film to prevent dehydration of the ion exchange resin.

Yet another embodiment is all organic MEMS devices, such as all organic micro-pumps, micro-valves and similar micro-actuators, particularly preferred for biomedical applications.

Working Principles of IP$^2$C Transducers

Actuator Mode

When a voltage is applied across the ionomeric core sheet of ion exchange resin, sandwiched between the positive electrode layer (anode) and the negative electrode layer (cathode) (i.e., the composite flexible membrane or briefly the "membrane" in the context of the present disclosure), the flexible composite membrane inflects towards the anode side (positive electrode) and its bending increases with the amplitude of the applied voltage. The deformation results from two distinct contributions. The first one is due a shift of the hydration shell of water molecules of the migrating ions within the ion exchange resin. When a voltage is applied to the electrodes, cations that are free to move in the ion exchange resin, migrate towards the cathode "carrying with them" a shell of water molecules of hydration. In this way the ion exchange resin closer to the cathode swells (expands) while the resin closer to the anode shrinks (contracts). The end result is an inflection force of a membrane strip towards the anode side. A second contribution to such a deformation, when a voltage is applied, is believed to depend from electrical charges distributions at the electrode/ion exchange resin interfaces due to Coulombian interactions between charges in the organic electrodes and the negative fixed charged groups of the polymer latticework (for the case of a cation exchange resin such as Nafion) and thus it depends on the characteristics of the organic electrode layers that are coupled to the ion exchange resin of the core sheet.

Sensor Mode

The membrane deformation besides remaining substantially reversible in time, appears to be reciprocal. Therefore, when the membrane is mechanically deformed a voltage is produced at the electrodes. When the membrane is deformed the resin closer to the inflection side is subject to a compression and the resin closer to the out-flexed side is subject to a correspondent expansion. This volumetric variation causes a corresponding variation of the respective densities of electrical charges at the opposite surfaces. The expanded side will be characterized by a lowered density of fixed negative charges, while the shrunk side will be characterized by an increased density of fixed negative charges. Thus the mobile cations will migrate toward the region of lower negative fixed charge density. This produces a voltage gradient that can be measured on the organic electrodes. This property results in a sensing capability and therefore the devices can be used as motion sensors.

Integration of All Organic Electronics

The development of "post-silicon" technologies based on the use of organic materials permit to realize integrated circuits with unusual properties of mechanical flexibility, light weight and enhanced disposability.

The basic building block of all organic electronics is the organic thin film transistor (OTFT). The basic materials that can be used to realize an OTFT are:

the organic semiconductor, for example chosen among: P3HT (Poly3-HexylThiophene), F8T2, PTAA, pentacene;

the organic conductor, for example chosen among: PEDOT:PSS (poly(3,4-ethylenedioxythiophene) doped with polystyrene sulfonate), Polyaniline (PANI), Polypyrrole etc.;

the organic dielectric and resist, for example chosen among: PMMA, Polystyrene, Polyimide (PI), PVP (Poly-4-vinylphenol), PHEMA (Poly(2-hydroxyethylmethacrylate) and PVAc (polyvinylacetate).

Of course the above identified organic materials do not represent exhaustively all the usable materials, other organic materials of equivalent electrical, mechanical and processability properties may be used.

Figure 7:
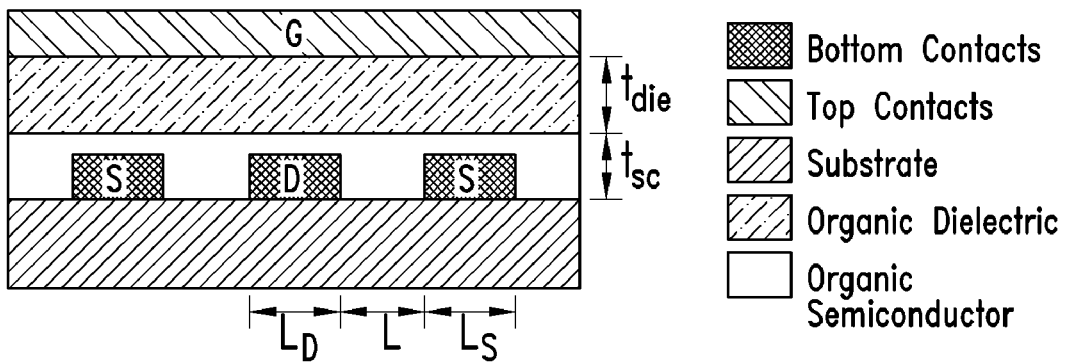
FIG. 7 shows a basic stack of organic filler layers required for realizing an OTFT active device.

Active(OTFT) and passive (organic thin film resistors and organic thin film capacitors) circuit components are realized through sequential deposition and patterning of the layers. The transistor is realized through the deposition and definition of successive layers for obtaining a multilayer structure as shown in FIG. 7.

Many architectures can be used to realize a multilayer OTFT, with the coupling of either the gate, source or drain contact to the proper substrate: Bottom gate-Top Contacts, Top Gate-Top contacts, etc. FIG. 7 is a sectional view of a so-called Top gate-Bottom contacts structure.

Figure 8:
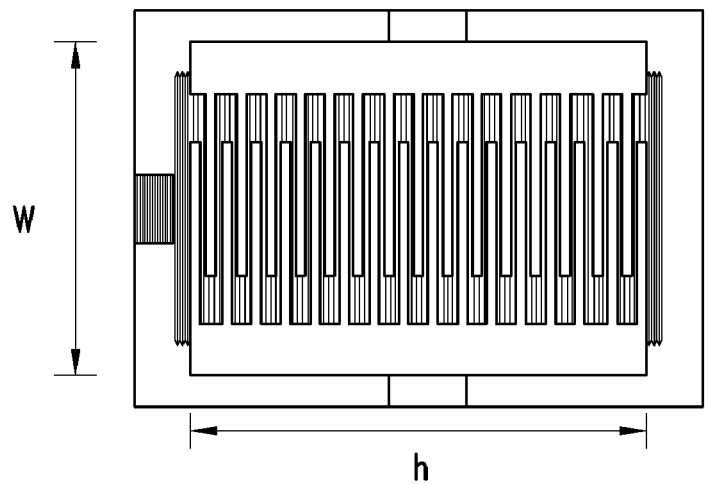
FIG. 8 is a layout view of interdigitated integrated structure of an OTFT.

In order to obtain a desired channel width, a multifinger structure with layout as depicted in FIG. 8 is normally realized.

Although at present electron-transporting n-type organic semiconducting materials are yet too sensitive to environmental conditions and for the prototype structures realized for testing only p-type organic semiconducting materials were used, availability of more reliable n-type organic semiconductors will make more efficient all organic CMOS circuitries of the sensor a viable alternative to the use of only p-type circuital structures.

Figure 9A:
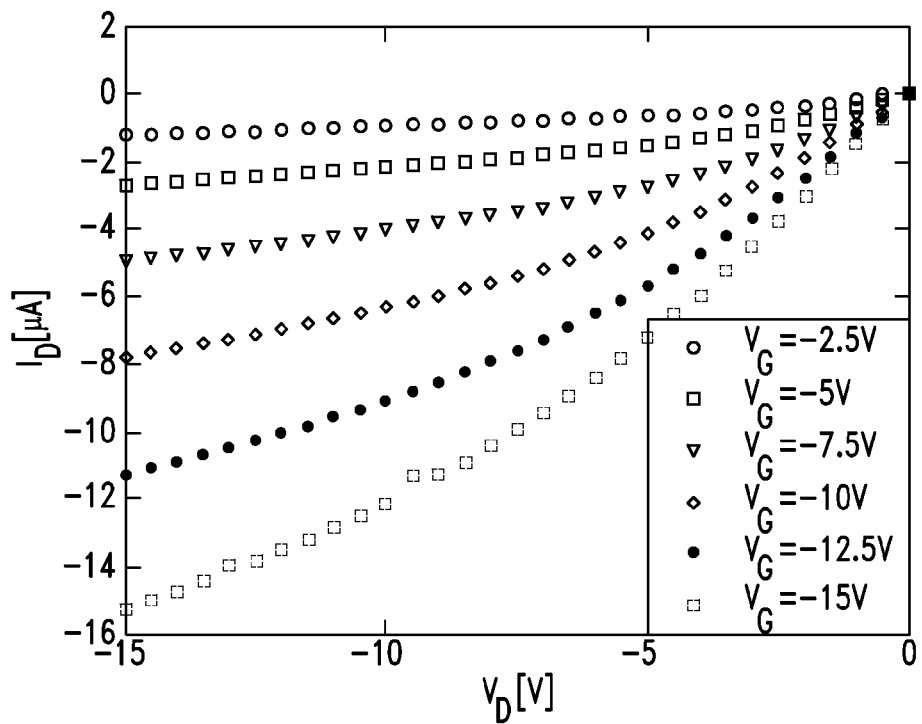
FIG. 9(a) and FIG. 9(b) show output and transfer characteristics of a P-type OTFT.
Figure 9B:
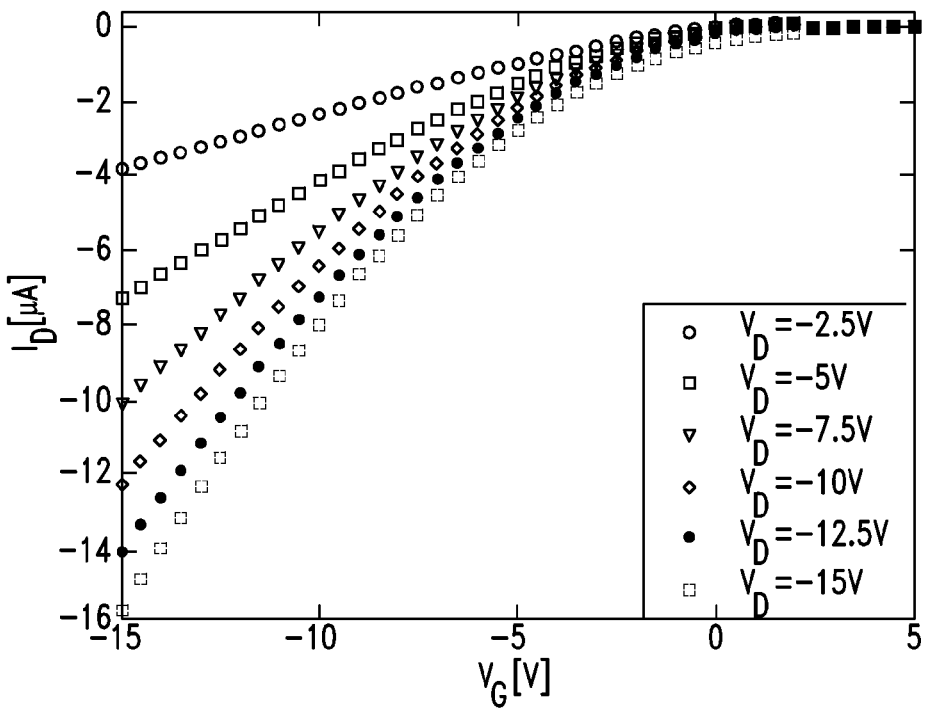

Typical output and transfer curves, of a p-type OTFT are shown in FIG. 9(a) and FIG. 9(b) respectively.

Figure 10A:
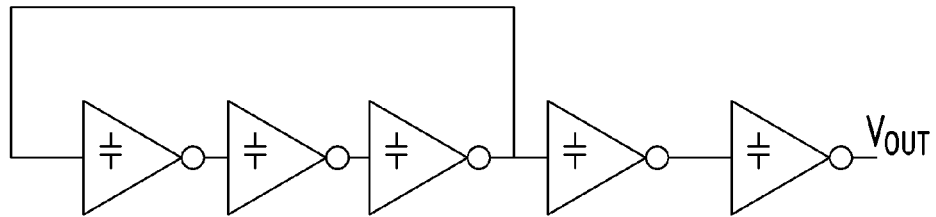
FIG. 10(a) and FIG. 10(b) are circuit diagram and layout of an all-organic ring-oscillator.
Figure 10B:
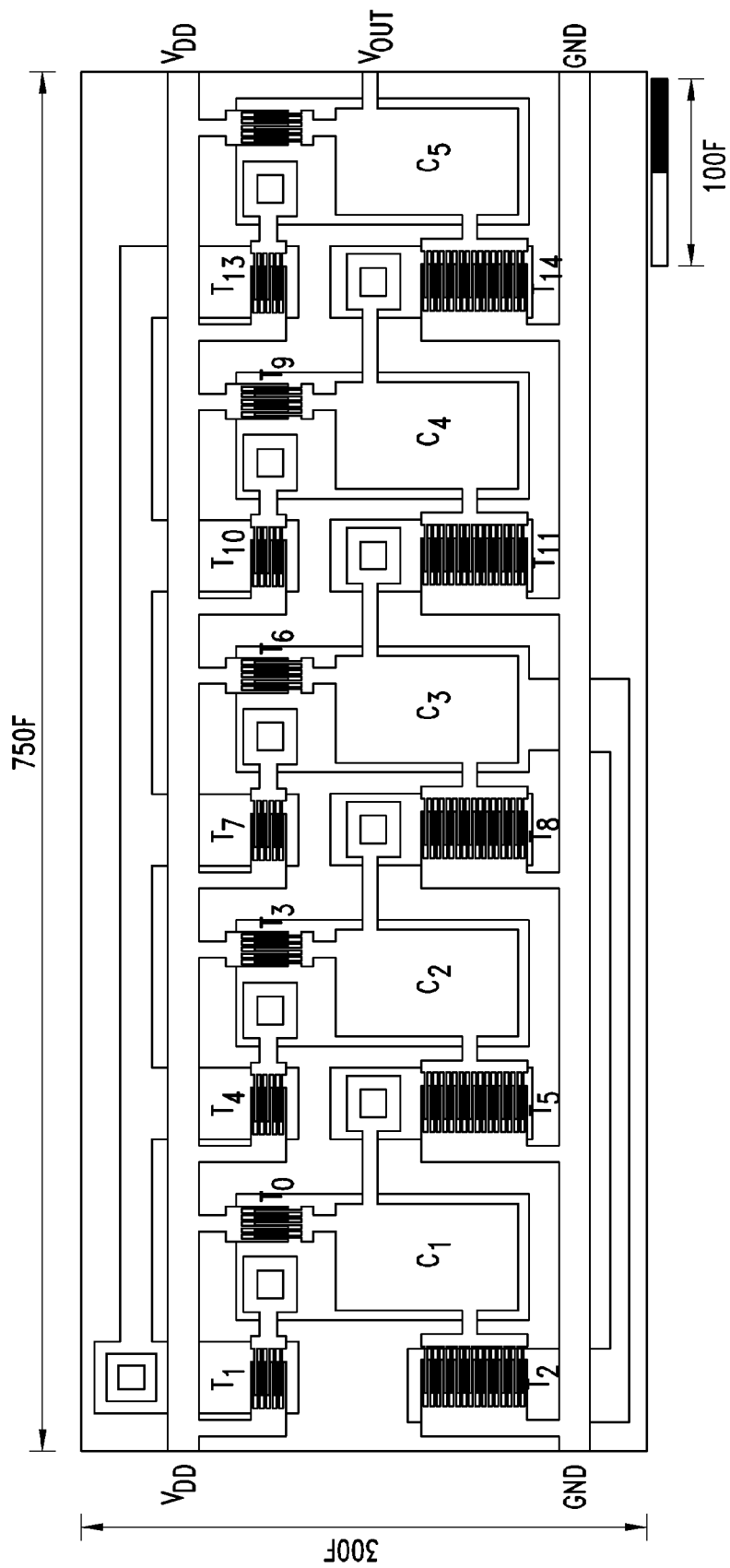

An organic ring-oscillator realized with rationed logic stages as depicted in FIG. 10(a) and in its layout picture of FIG. 10(b) may be used to generate a suitable drive signal to be applied to the electrodes of an IP$^2$C actuator in order to obtain a desired reciprocating motion of the sensible flexible membrane.

Figure 11:
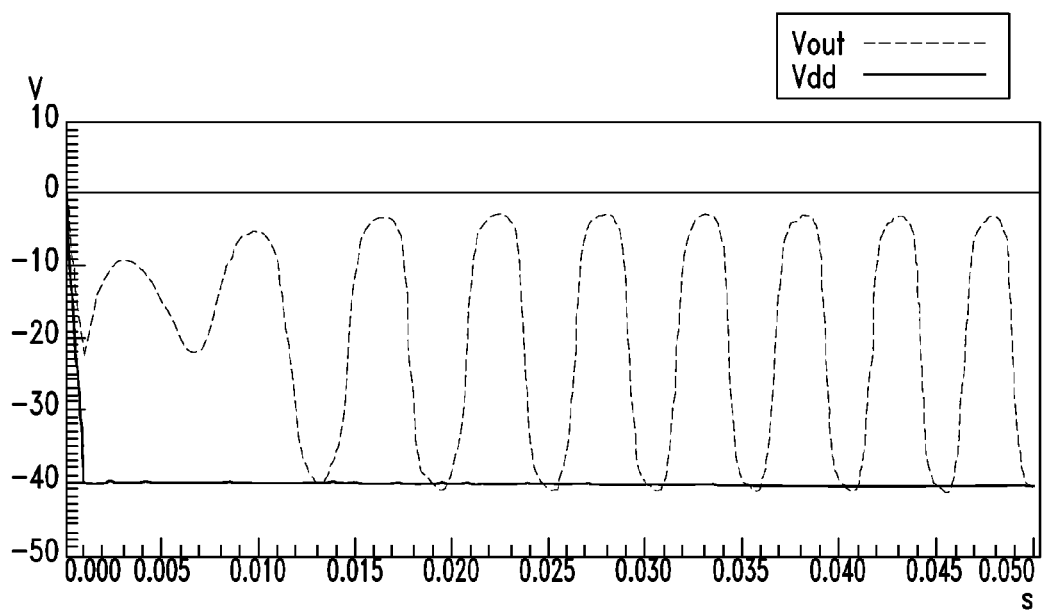
FIG. 11 shows a typical output signal of the ring oscillator of FIG. 10.

A typical output signal of a ring oscillator of FIG. 10 is shown in FIG. 11.

Figure 12:
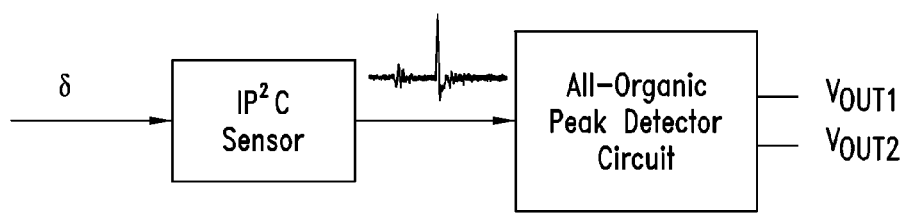
FIG. 12 is a block diagram of the functional circuit of an organic integrated sensor according to an embodiment of this disclosure.

FIG. 12 is a block diagram of the functional circuit of an all organic integrated sensor according to an embodiment of the present disclosure.

When the flexible sensible multilayer membrane IP$^2$C sensor is subjected to a displacement ($\delta$), it generates a sequence of current peaks that are detected by an all organic, peak detection circuit, which produces two digital voltage outputs, $V_{out1}$ and $V_{out2}$.

Figure 13A:
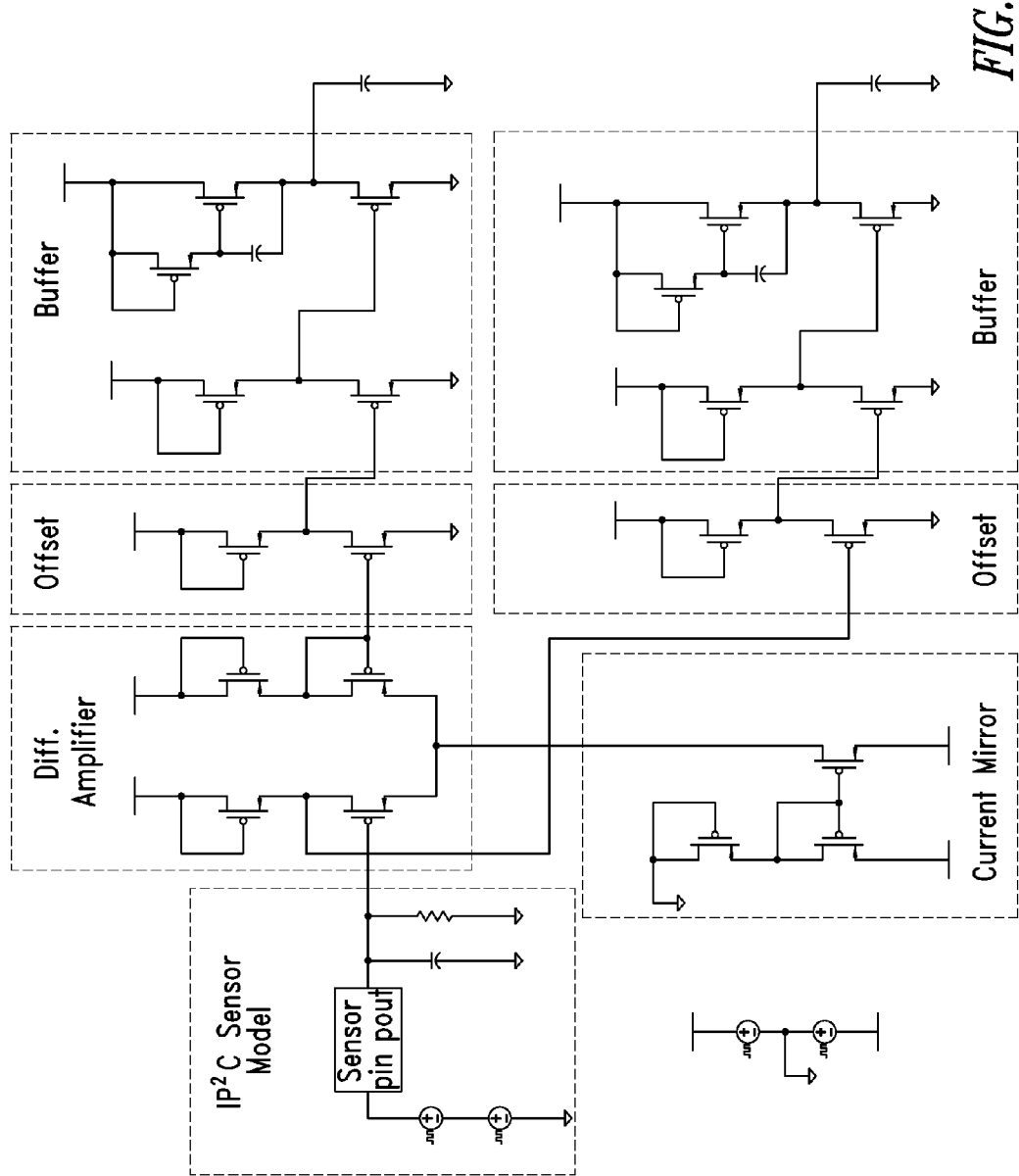
FIG. 13(a) is a detail circuit of an all-organic peak detector circuit.

A detailed circuit of the all-organic peak detector circuit is shown in FIG. 13(a). It is based on a differential amplifier stage and two separate common source amplifier blocks. To each amplifier block is associated an offset regulation input stage and a non-inverting buffer stage.

Figure 13B:
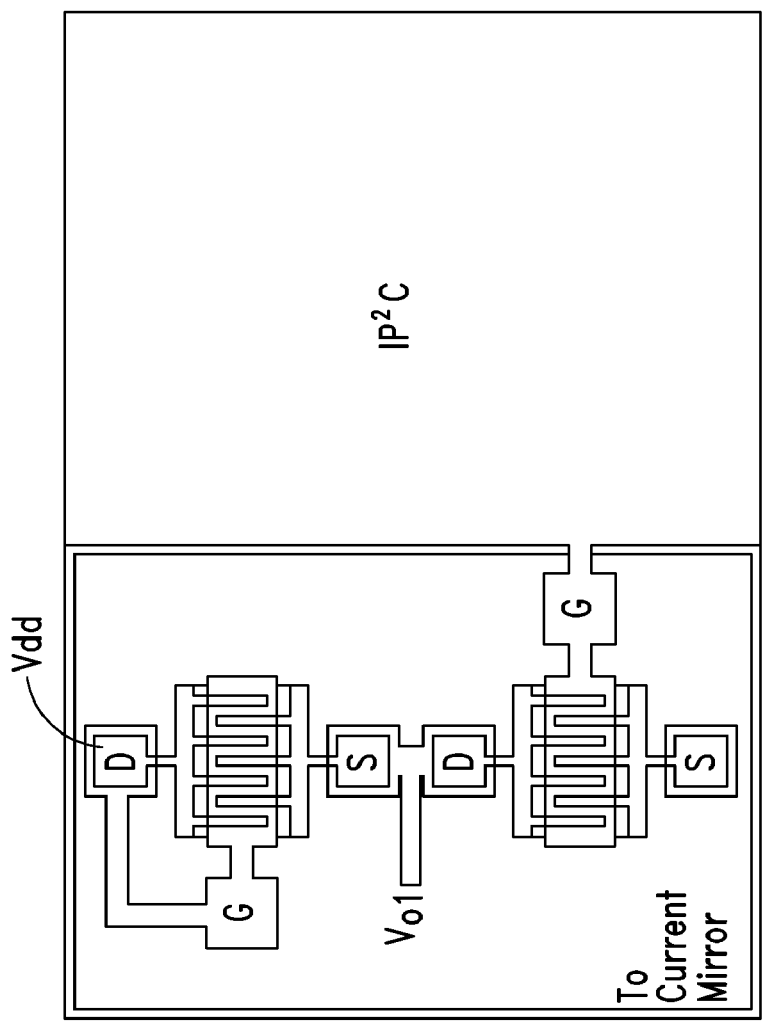
FIG. 13(b) is a layout view of the left side input transistors of the differential amplifier of the circuit of FIG. 13(a), coupled to the $IP^2C$ sensor.

The current peaks passing through the RC circuits are detected by the differential amplifier producing two output signals of opposite value. FIG. 13(b) is a layout view of the left side input devices of the differential amplifier coupled to the IP²C sensor of the detailed circuit of FIG. 13(a). The output signals are amplified by each of the two amplification stages producing two delayed output voltage pulses $V_{OUT1}$ and $V_{OUT2}$.

Figure 14A:
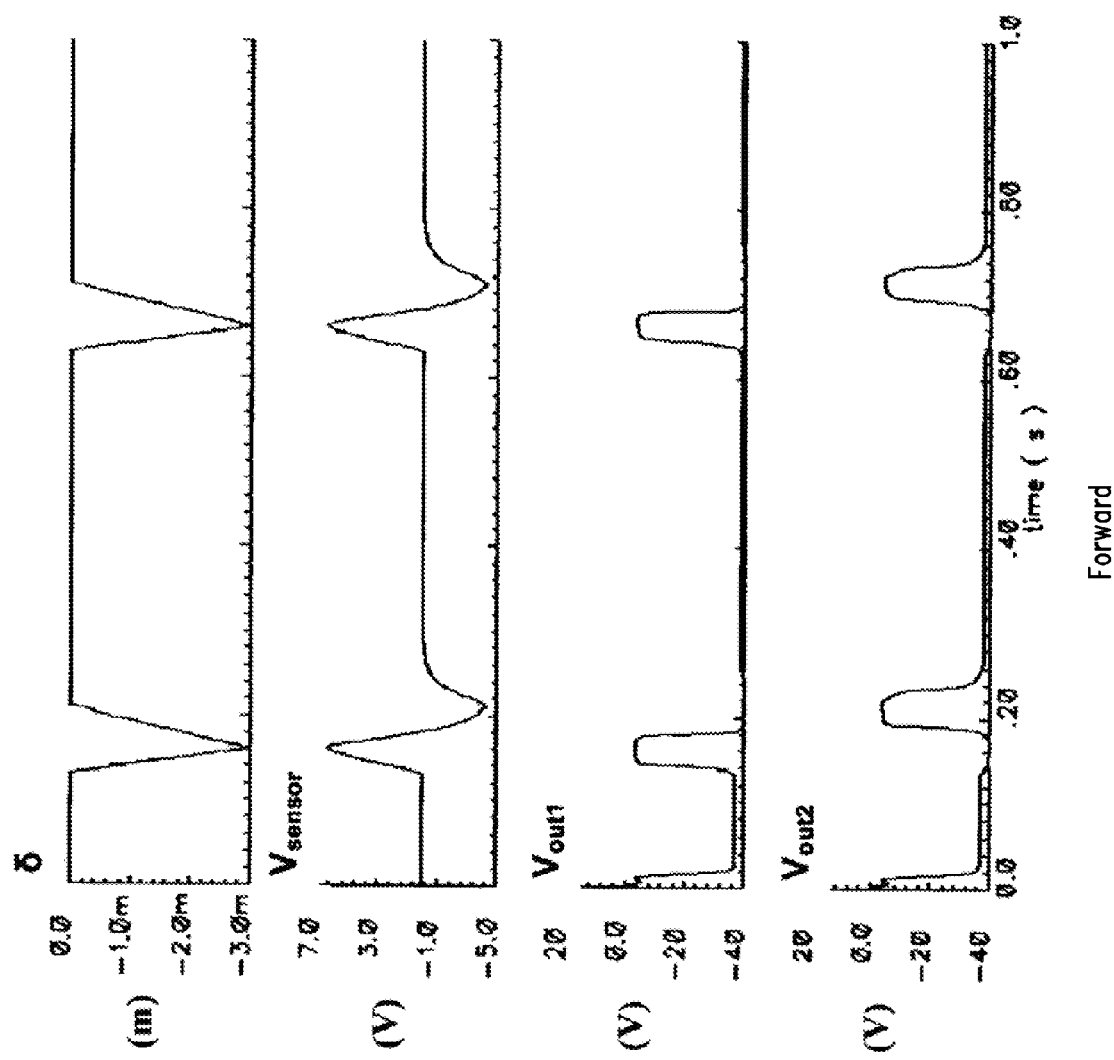
FIG. 14(*a*) and FIG. 14(*b*) are simulation results of an IP²C sensor of FIG. 12 for a forward displacement and for a backward displacement, respectively.
Figure 14B:
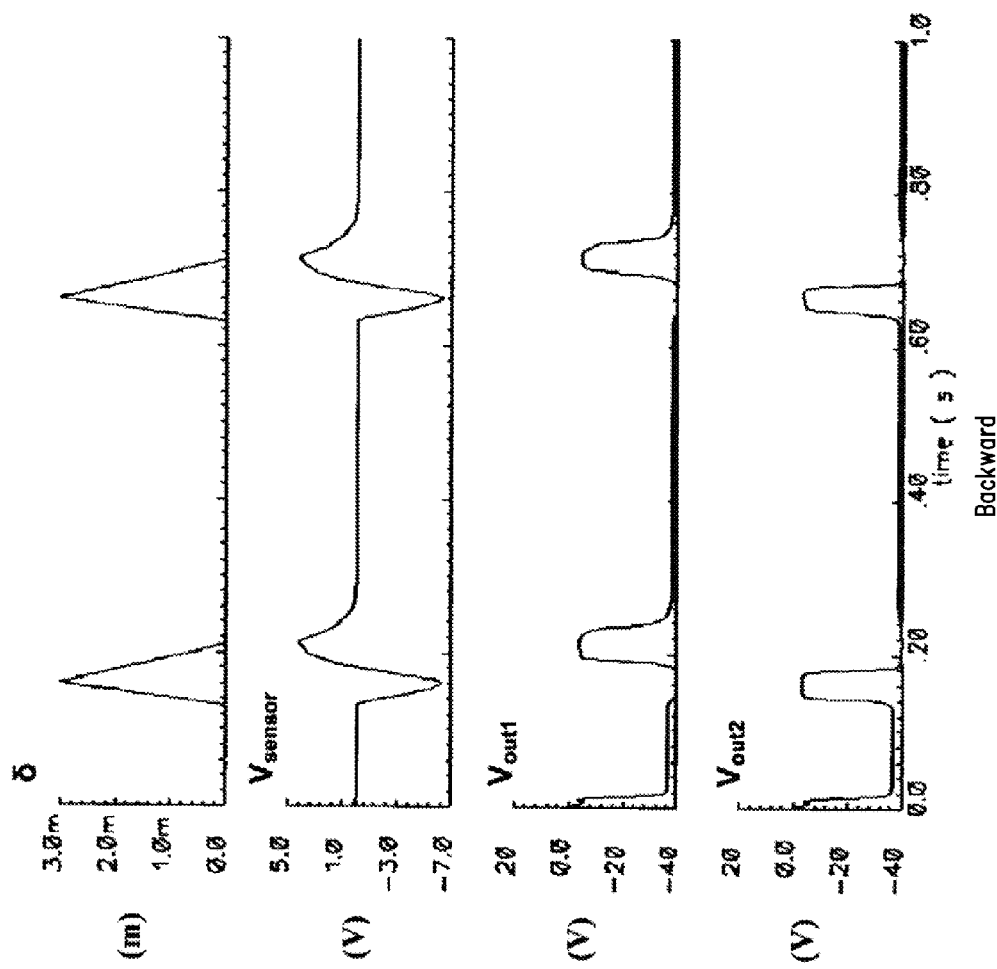

The IP²C sensor and the organic peak detector circuit have been developed under Cadence DFII environment and the entire circuit has been simulated by means of Mentor Graphics ELDO. Simulation results are reported in FIG. 14(a) and FIG. 14(b). If a "forward" (conventionally in a negative direction) displacement occurs (FIG. 14(a)), the pulse produced at the second output ($V_{OUT2}$) is delayed in respect to the first output ($V_{OUT1}$). If a "backward" (conventionally in a positive direction) displacement occurs (FIG. 14(b)), it is the pulse that is produced at the first output ($V_{OUT1}$) to be delayed in respect to the second output ($V_{OUT2}$).

The produced output signals well-match with organic digital circuits capable of computing the information produced by the peak detection circuit to implement complex sensing information. For example, a set of IP²C sensors, each coupled with its peak detection circuit, can be used to implement complex all organic motion sensing systems, useful for example, as forward/backward incremental encoders.

Active Device Structures

Figure 15:
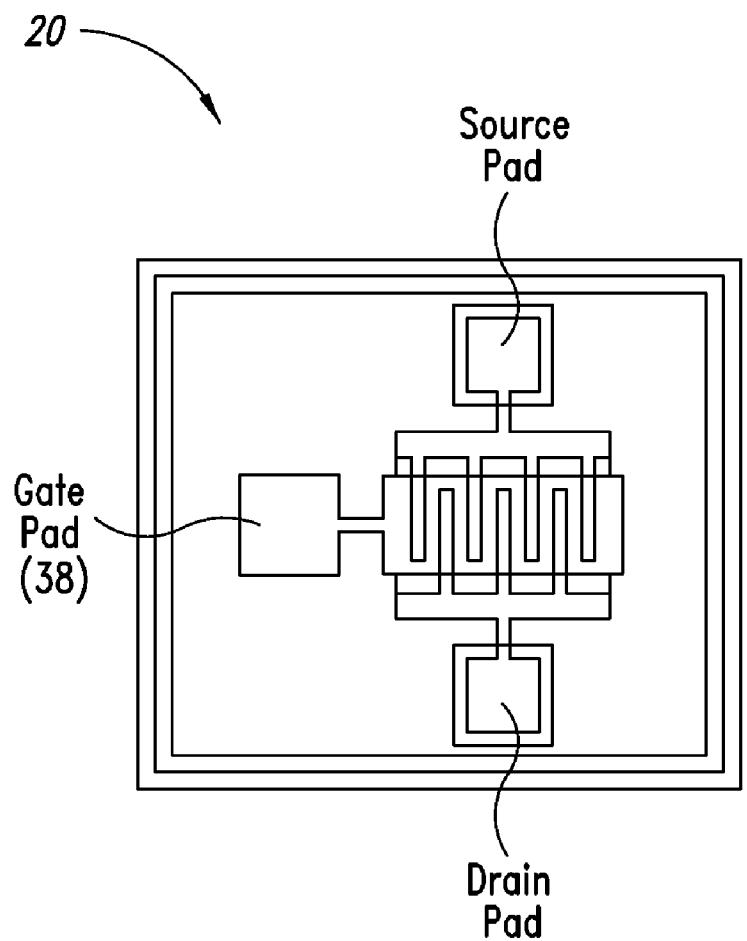
FIG. 15 is a layout view of an OTFT device.
Figure 16:
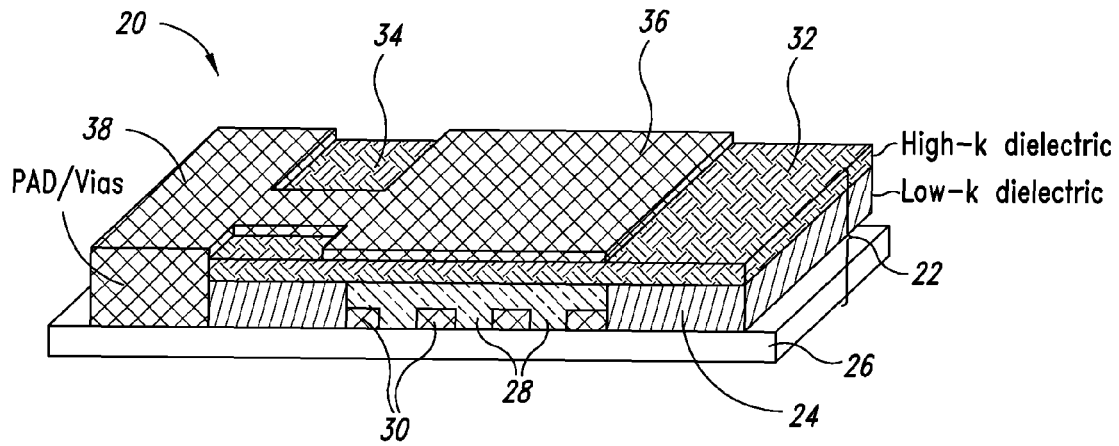
FIG. 16 is a sectional view in the section plane indicated in FIG. 15.

Another exemplary layout view of an OTFT device 20 is shown in FIG. 15 and a cross sectional tridimensional view is shown in FIG. 16. The OTFT device 20 includes a multilayer stack 22 of organic layers. The multilayer stack 22 includes an organic dielectric buffer layer 24 on a substrate 26, a semiconductive organic polymeric layer 28, a first patterned conductive polymeric filler layer 30, a dielectric organic polymer layer 32, and a second patterned conductive polymeric filler layer 34. The substrate 26 can be a circuit portion of the core sheet 1 of one of the sensors or actuators discussed above. The semiconductive organic polymeric layer 28 is formed in said buffer layer 24 and is defined to provide an active area for the OTFT device 20. The first patterned conductive polymeric filler layer 30 is provided for realizing source and drain contacts in said defined semiconductive organic polymeric layer 28. The dielectric organic polymer layer 32 is over said defined areas of said semiconductive organic polymeric layer to provide a gate dielectric for the OTFT device 20. The second patterned conductive polymeric filler layer 34 is defined to constitute a gate electrode 36 over said dielectric organic polymer layer 32 and said defined areas of the semiconductive organic polymeric layer 28 and a gate pad 38 of the OTFT device 20.

The OTFT device 20 of FIGS. 15 and 16 could be used to implement any of the OTFT devices discussed above, including any of the transistors shown in FIGS. 13(a) and 13(b). The first patterned conductive polymeric filler layer 30 can generally be used to provide first plates of integrated capacitors, first integrated resistors, and first electrical connection lines. The second patterned conductive polymeric filler layer 34 can generally be defined to provide second plates of said integrated capacitors, second integrated resistors and second electrical connection lines. For example, with respect to the circuits of FIGS. 13(a), (b), the first patterned conductive polymeric filler layer 30 can also be used to provide bottom plates of the integrated capacitors, the integrated resistor, and any of the electrical connection lines, particularly those coupled to the bottom plates. Similarly, the second patterned conductive polymeric filler layer 34 can be defined to provide the top plates of the integrated capacitors, the integrated resistor, and any of the electrical connection lines, particularly those coupled to the top plates.

Figure 17:
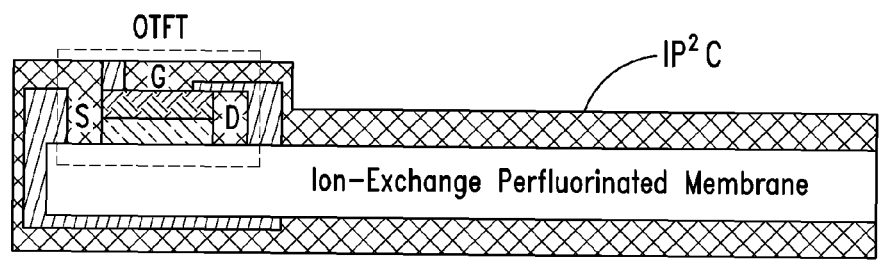
FIG. 17 is a cross sectional view of an IP²C sensor and of an OTFT device coupled to the IP²C structure for sensing a voltage difference between the conductive organic electrodes of the sensing element.

FIG. 17 is a cross sectional view of a transducer device 200 that includes a sensor, such as the IP2C sensor 100A of FIG. 5, or an actuator, such as the IP2C actuator 100B of FIG. 6, and of an OTFT device, such as the OTFT device 20 of FIGS. 15-16. In practice, the OTFT device 20 can be coupled to the IP2C sensor 100A for sensing a voltage difference between the conductive organic electrodes 2 and 3 of the sensing element (IP2C). The OTFT device 20 is integrated on an end portion of the core sheet 1 of the elongated sensor and may be one of the input devices of the differential amplifier of FIG. 13(a).

Figure 18:
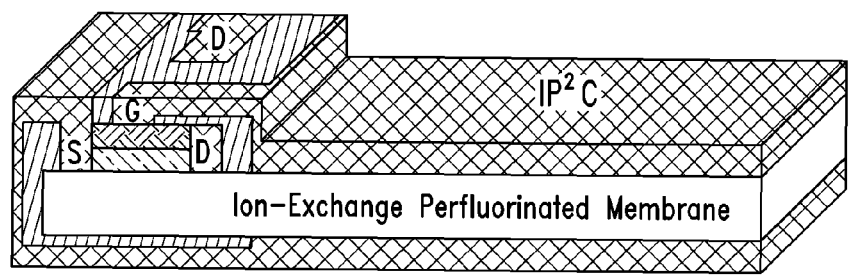
FIG. 18 is a three-dimensional view of the cross sectional view of FIG. 17, showing the location of the vias for contacting the drain electrode of the OTFT structure.
Figure 18:
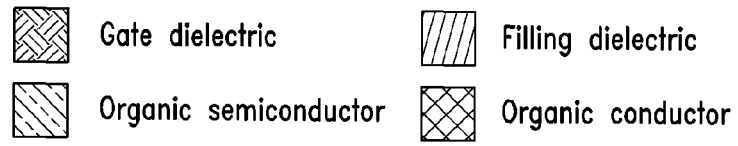

FIG. 18 is a tridimensional view of a cross section of FIG. 17 showing the location of the vias that is realized in order to contact the drain; the source and the gate being connected to the opposite electrodes of the IP2C sensor.

Although they are not shown in FIGS. 17 and 18, the transducer device includes 200 includes a power source for powering the device and an input/output circuit. The power source can include the micro battery 7 of FIG. 5 and the input/output circuit can input the OLED 8 of FIG. 5. The input/output circuit would typically include an ON/OFF circuit for switching on/off the organic transducer. If the transducer device 200 includes an IP2C actuator like that of FIG. 6, the input/output circuit would also include a control circuit for controlling actuator functioning. If the transducer device 200 includes an IP2C sensor like that of FIG. 5, the input/output circuit would also include an output circuit for outputting information gathered by the sensing element.

The various embodiments described above can be combined to provide further embodiments. All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic transducer, comprising:
 a transducing element that includes:
  a flexible core sheet of an ion exchange organic material;
  a first electrically conductive flexible layer of an electrically conductive organic material coupled to a first major surface of the sheet; and
  a second electrically conductive flexible layer of an electrically conductive organic material coupled to a second major surface of the sheet, the second major surface being opposite to the first major surface; and
 a transistor formed in a multilayer stack, the multilayer stack including:
  a semiconductive organic polymeric layer on a portion of the sheet, the semiconductive organic polymeric layer including an active area;
  a first patterned conductive polymeric filler layer for realizing source and drain contacts in contact with said semiconductive organic polymeric layer;
  a dielectric organic polymer layer over said active area of said semiconductive organic polymeric layer; and
  a second patterned conductive polymeric filler layer constituting a gate electrode over said dielectric organic polymer layer and said active area of the semiconductive organic polymeric layer.

2. The transducer of claim 1, wherein said core sheet is of a hydrated polymer having fixed pendant polar groups.

3. The transducer of claim 1, wherein said electrically conductive flexible layers are of a material belonging to the group composed of poly(3,4-ethylenedioxythiophene) doped with polystyrene sulfonate, polyaniline, polypyrrole and mixtures thereof.

4. The transducer of claim 1, wherein the transducing element is a sensor.

5. The transducer of claim 1, wherein the source and drain contacts include a plurality of source contacts and a plurality of drain contacts that are interleaved with the source contacts.

6. The transducer of claim 1, wherein the multilayer stack includes an organic dielectric buffer layer on the portion of said core sheet, the semiconductive organic polymeric layer being positioned within the organic dielectric buffer layer.

7. The transducer of claim 1, further comprising an organic battery coupled to the transducing element.

8. The organic transducer of claim 1, further comprising an all organic input/output element configured to control the transducing element.

9. The transducer of claim 1, wherein the semiconductive organic polymeric layer of the transistor has a bottom surface that directly contacts a top surface of the sheet.

10. An organic transducer, comprising:
a transducing element that includes a core sheet of an ion exchange organic material, and first and second electrically conductive layers each of an electrically conductive organic material, at least part of the sheet being sandwiched between the first and second electrically conductive layers, the first electrically conductive layer being coupled to a first major surface of the sheet and the second electrically conductive layer being coupled to a second major surface of the sheet that is opposite to the first major surface;
a functional circuit defined in an organic multilayer stack at least partly over a dedicated area of the sensing element, the multilayer stack including:
an organic dielectric buffer layer on a circuit portion of said core sheet;
a semiconductive organic polymeric layer over said buffer layer, the semiconductive organic polymeric layer including defined areas of active circuital components;
a first patterned conductive polymeric filler layer for realizing source and drain contacts with said defined semiconductive organic polymeric layer, first plates of integrated capacitors, first integrated resistors, and first electrical connection lines;
a dielectric organic polymer layer over said defined areas of said semiconductive organic polymeric layer; and
a second patterned conductive polymeric filler layer constituting gate electrodes over said dielectric organic polymer layer and said defined areas of the semiconductive organic polymeric layer, second plates of said integrated capacitors, second integrated resistors and second electrical connection lines; and
a power source for powering said functional circuit, the power source including a micro battery coupled to the functional circuit.

11. The organic transducer of claim 10, wherein an isolation and/or environment-compatible flexible film of an organic material completely encapsulates the organic transducer.

12. The organic transducer of claim 10, further comprising input/output means for controlling the transducing element, wherein the input/output means are all organic optical devices.

13. The organic transducer of claim 10, wherein said semiconductive organic polymeric layer is of a material belonging to the group composed of Poly3-HexylThiophene, F8T2, PTAA and pentacene.

14. The organic transducer of claim 10, wherein said dielectric organic polymer belongs to the group composed of PMMA, polystyrene, polyimide, poly-4-vinylphenol, poly (2-hydroxyethyl-methacrylate), and polyvinylacetate.

15. The organic transducer of claim 10, wherein said conductive polymeric filler layers are of a material belonging to the group composed of poly(3,4-ethylenedioxythiophene) doped with polystyrene sulfonate, polyaniline, polypyrrole and mixtures thereof.

16. The organic transducer of claim 10, wherein the transducing device is an actuator.

17. An organic transducer, comprising:
a transducing element that includes:
a flexible core sheet of an ion exchange organic material;
a first electrically conductive flexible layer of an electrically conductive organic material coupled to a first major surface of the sheet;
a second electrically conductive flexible layer of an electrically conductive organic material coupled to opposite second major surface of the sheet opposite to the first major surface; and
a transistor including:
a semiconductive organic polymeric layer on a portion of the sheet, the semiconductive organic polymeric layer including an active area;
first and second conductive polymeric terminals in contact with said semiconductive organic polymeric layer; and
a conductive polymeric control terminal coupled to said active area of the semiconductive organic polymeric layer.

18. The transducer of claim 17, wherein said electrically conductive flexible layers are of a material belonging to the group composed of poly(3,4-ethylenedioxythiophene) doped with polystyrene sulfonate, polyaniline, polypyrrole and mixtures thereof.

19. The transducer of claim 17, wherein said transistor includes a dielectric organic polymer layer between said active area of said semiconductive organic polymeric layer and said control terminal.

20. The transducer of claim 17, wherein the first conductive polymeric terminal includes a plurality of source contacts and the second conductive polymeric terminal includes a plurality of drain contact that are interleaved with the source contacts.

21. The transducer of claim 17, further comprising an organic dielectric buffer layer on the portion of said core sheet, the semiconductive organic polymeric layer being positioned within the organic dielectric buffer layer.

22. The transducer of claim 17, wherein the semiconductive organic polymeric layer of the transistor has a bottom surface that directly contacts a top surface of the sheet.

* * * * *